US00PP21282P3

(12) United States Plant Patent
Egger

(10) Patent No.: US PP21,282 P3
(45) Date of Patent: Sep. 7, 2010

(54) ***TIARELLA* PLANT NAMED 'MYSTIC MIST'**

(50) Latin Name: *Tiarella*
Varietal Denomination: Mystic Mist

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/231,835

(22) Filed: Sep. 5, 2008

(65) Prior Publication Data

US 2010/0064403 P1 Mar. 11, 2010

(51) Int. Cl.
*A01H 5/00* (2006.01)

(52) U.S. Cl. ..... Plt./486

(58) Field of Classification Search ..... Plt./486
See application file for complete search history.

(56) References Cited

U.S. PATENT DOCUMENTS

PP15,528 P2 * 2/2005 Heims et al. ..... Plt./486

OTHER PUBLICATIONS

UPOV ROM GTITM Computer Database, GTI Jouve Retrieval Software 2009/03 Citation for 'Mystic Mist'.*

* cited by examiner

*Primary Examiner*—Wendy C Haas
(74) *Attorney, Agent, or Firm*—Klarquist Sparkman, LLP

(57) ABSTRACT

A new and distinct hybrid of *Tiarella* plant characterized by excellent vigor; a stable uniform speckled variegation; prominent maroon markings along main veins; pink buds to white flowers on pink flowering stems; and a compact habit.

2 Drawing Sheets

Botanical denomination: *Tiarella* spp.
Variety designation: 'Mystic Mist'.
Parentage: *Tiarella wherryi*×*Tiarella*.spp. massed.

BACKGROUND OF THE INVENTION

The present invention relates to a new and distinct cultivar of *Tiarella* and given the cultivar name of 'Mystic Mist'. *Tiarella* is in the family Saxifragaceae. The new cultivar originated from a planned breeding program to create a vigorous variegated *Tiarella* using *Tiarella wherryi* 'Heronswood Mist' (an unpatented plant), as the seed parent, and a mass of selected proprietary *Tiarella* hybrids, as the pollen parents. Offspring were selected and line crossed and the most attractive vigorous and variegated plants were grown out for evaluation. *Tiarella* 'Mystic Mist' was selected as superior.

SUMMARY OF THE INVENTION

This new *Tiarella* is distinguished by:

1. excellent vigor,
2. a stable uniform speckled variegation,
3. prominent maroon markings along main veins,
4. pink buds to white flowers on pink flowering stems, and
5. a compact habit.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The new variety has not been evaluated under all possible environmental conditions. The phenotype may change with variations in environment without a change in the genotype of the plant.

DETAILED PLANT DESCRIPTION

Figure 1:
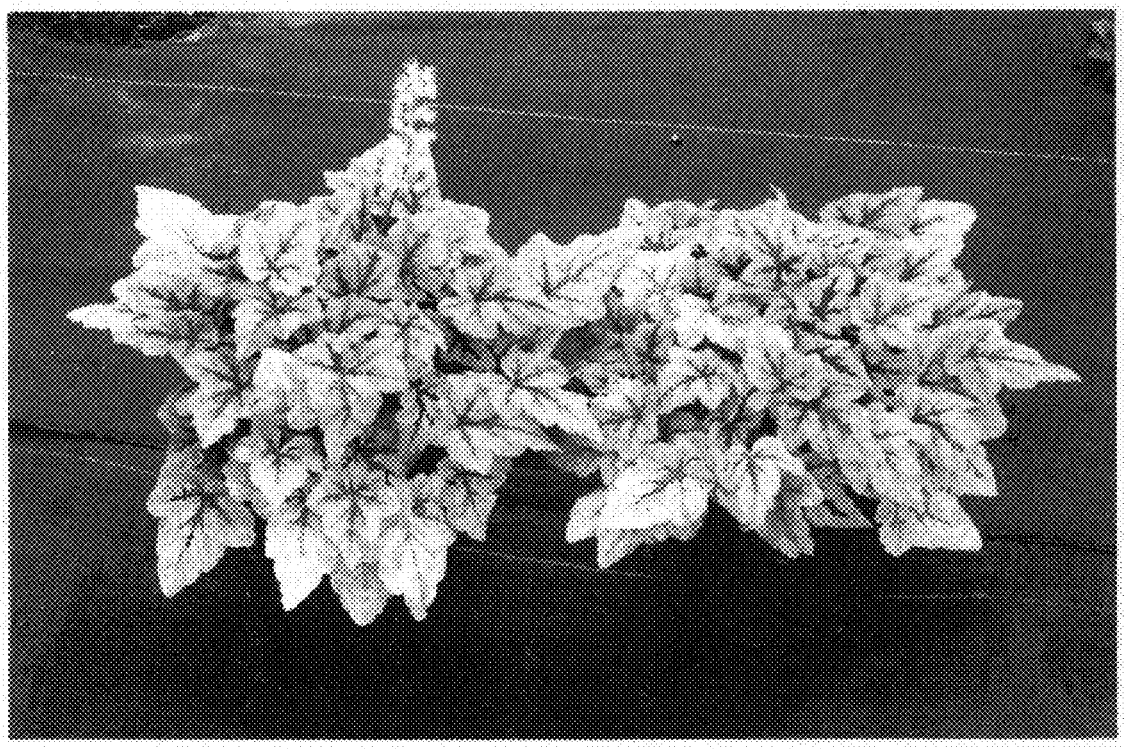
FIG. 1 shows a one gallon *Tiarella* 'Mystic Mist' with the spring and summer foliage color (and one raceme with flowers) on the left and with winter foliage color on the right, growing in a one gallon container in Canby, Oreg.
Figure 2:
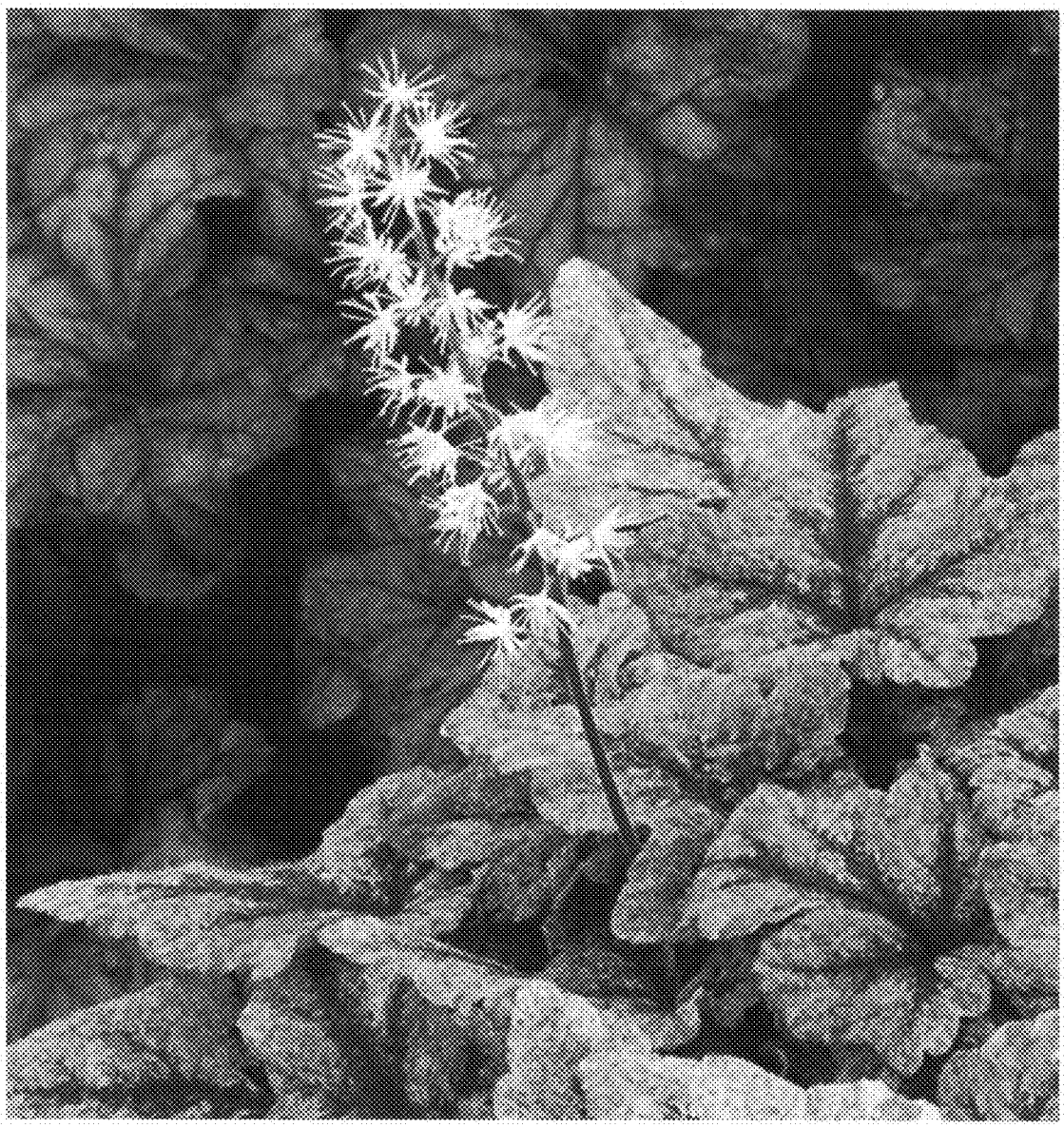
FIG. 2 shows a close-up of the flower of *Tiarella* 'Mystic Mist'.

The following is a detailed description of the new *Tiarella* hybrid based on observations of two-year-old specimen grown in a one gallon container in a cool greenhouse in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:

*Type.*—Herbaceous perennial.
*Hardiness.*—USDA Zones 4 to 9.
*Size.*—27 cm wide and 12 cm tall.
*Form.*—Clumping.
*Vigor.*—Excellent.
*Roots.*—Fibrous, white; propagates easily from crown divisions.

Leaf:

*Type.*—Simple.
*Shape.*—Ovate.
*Lobing.*—5 pinnate lobes, with the terminal lobe growing to 5 cm long and 5 cm wide.

*Arrangement.*—Rosette.
*Blade length.*—Grows to 9 cm long.
*Blade width.*—7.3 cm at widest point.
*Margins.*—Broadly crenate.
*Apex.*—Acute.
*Base.*—Cordate.
*Venation.*—Palmate.
*Surface texture.*—Hispid on both sides.
*Petiole description.*—7 to 10.5 cm, hispid, Greyed Purple RHS 187B, lighter with maturity.
*Color.*—Spring and summer topside Yellow Green (RHS 146A to RHS 144A) with variegation Yellow RHS 4D and maroon around veins Greyed Purple RHS 187B; bottom side Yellow Green RHS 147B to RHS 147C; in winter Green RHS 137A with the creamy variegated areas tinted pink, Greyed Purple 186D and oldest leaves darken to a color closest to Greyed Purple RHS 187B with veins Greyed Purple RHS 187A.

Inflorescence:
*Type.*—Raceme.
*Number of flowers per raceme.*—25 to 35.
*Number of inflorescences in first spring flush.*—12.
*Peduncle.*—Unbranched, 22 cm long, 2 mm wide, hispid, with 0 or 1 leafy bracts.
*Color.*—Closest to Greyed Purple RHS 186C.
*Pedicel.*—7 mm long, glandular, Brown RHS 200B, color closest to Greyed Purple RHS 186C.
*Lastingness.*—Each raceme lasts for about 3 weeks.

Flower bud:
*Size.*—3 mm deep and 2 mm wide.
*Shape.*—Ovoid, down facing until open.
*Surface texture.*—Glandular.
*Color.*—Pink, Red Purple RHS 69A.

Flower:
*Type.*—Perfect, actinomorphic, sepals petaloid.
*Flower description.*—Rotate, 6 mm deep and 11 mm wide including stamen.
*Corolla description.*—Rotate, 3 mm deep and 9 mm wide; each of five petals ovate to lanceolate with a clawed base, with margins incised, apex acuminate, base cuneate, grows to 5.5 mm long and 2.5 mm wide, White RHS 155C and glabrous inside and out.
*Calyx description.*—5 parted, petaloid, parted almost to the base, rotate, 6 mm wide and 3 mm deep; each sepal lobe 3 mm long and 1.3 mm wide, oblanceolate, acute, White RHS 155A on both sides, glabrous inside and glandular on backs.
*Pistil description.*—One, 5 mm long, White RHS 155A overall, ovary 2 mm deep, style 3 mm long.
*Stamen description.*—Anthers 10 in number, conspicuously exerted, filaments 4 mm long, White RHS 155A, anthers 1 mm long and Orange RHS 28C, pollen Yellow Orange RHS 22A.
*Bloom period.*—April to May in Canby, Oreg.
*Fragrance.*—None.

Fruit:
*Type.*—A one-celled capsule, beak-like, composed of two unequal parts.
*Size.*—0.7 cm long.
*Color.*—Brown RHS 200C.

Seeds:
*Color.*—Black RHS 202A.
*Shape.*—Minute, oval, 1 mm long.
*Fertility.*—Fertile.

Pest and diseases: This new hybrid shows good mildew tolerance, the main problem for *Tiarella*. No major pest problems. It is susceptible to root weevils like all *Tiarella*.

Comparisons to similar *Tiarella*: Compared to *Tiarella wherryi* 'Heronswood Mist' (unpatented), one of the parent species, the new variety is more vigorous, and has stronger colored red veins.

I claim:

1. A new and distinct hybrid of *Tiarella* plant as herein illustrated and described.

* * * * *